United States Patent [19]

Rae

[11] Patent Number: 4,651,729

[45] Date of Patent: Mar. 24, 1987

[54] FLUID FLOW REGULATOR

[76] Inventor: Ronald D. Rae, Bromide St., Broken Hill, New South Wales, Australia

[21] Appl. No.: 798,152

[22] Filed: Nov. 15, 1985

Related U.S. Application Data

[63] Continuation of Ser. No. 518,290, Jul. 28, 1983, abandoned.

[30] Foreign Application Priority Data

Jul. 30, 1982 [AU] Australia .................... PF5146

[51] Int. Cl.$^4$ ............................................. A61M 16/00
[52] U.S. Cl. ........................... 128/203.14; 128/204.22; 128/203.28
[58] Field of Search ...................... 128/203.14, 204.21, 128/204.22, 204.23, 203.25, 205.13, 203.28; 137/93, 112, 114, 625.4

[56] References Cited

U.S. PATENT DOCUMENTS

| | | | |
|---|---|---|---|
| 2,323,675 | 7/1943 | Rand .................................. | 137/93 |
| 3,923,056 | 12/1975 | Bingmann et al. .............. | 128/204.21 |
| 4,150,670 | 4/1979 | Jewett et al. ................... | 128/204.22 |
| 4,204,536 | 5/1980 | Albamda ........................ | 128/203.25 |
| 4,215,409 | 7/1980 | Strowe .......................... | 128/203.14 |
| 4,232,666 | 7/1980 | Savelli et al. .................. | 128/203.25 |
| 4,284,103 | 8/1981 | Pemberton ..................... | 137/625.4 |
| 4,328,823 | 5/1982 | Schreiber ....................... | 128/203.25 |
| 4,340,044 | 7/1982 | Levy et al. ..................... | 128/204.21 |
| 4,345,612 | 8/1982 | Koni et al. ..................... | 128/203.14 |

FOREIGN PATENT DOCUMENTS 2006629  5/1979  United Kingdom .

OTHER PUBLICATIONS

Coles et al, "Computer Control of Respiration and Anesthesia", Medical and Biological Engr., (May 1973), pp. 262–267.

Westenskow et al, "Instrumentation for Measuring Continuous Oxygen Consumption of Surgical Patients", IEEE Transactions on Biomedical Engr., vol. BME-24, No. 4 (Jul. 1977), pp. 331–337.

*Primary Examiner*—Henry J. Recla
*Attorney, Agent, or Firm*—Birch, Stewart, Kolasch & Birch

[57] ABSTRACT

An anaesthetic gas flow regulator includes an oxygen gas flow line connected to a supply of oxygen, an anaesthesia gas flow line connected to a supply of anaesthesia gas, controllable valves connected to the oxygen and anaesthesia gas flow lines, a patient rebreathing circle for delivering and exhausting a mixture of oxygen and anaesthesia gas to and from the patient to a common outlet means, an oxygen analyzer and a gas volume analyzer. The oxygen analyzer senses the oxygen concentration of the mixture of oxygen and anaesthesia gas in the rebreathing circle, and provides an oxygen signal when a minimum predetermined oxygen concentration is sensed by the oxygen analyzer. The volume sensor generates a volume signal indicative of a minimum volume threshold value in the rebreathing circle. Control circuitry is provided responsive to the oxygen and volume signals developed by the oxygen analyzer and the volume sensor to supply a controlled amount of either oxygen or anesthesia gas to the rebreathing circle through the common outlet. The control circuit assures that the volume in the patient rebreathing circle is kept constant, and oxygen is delivered to the patient rebreathing circle only when a minimum predetermined signal is sensed by the oxygen analyzer, otherwise anaesthesia gas is delivered to the patient rebreathing circle to maintain the volume of gas flow therein substantially constant.

12 Claims, 21 Drawing Figures

FLUID FLOW REGULATOR

This application is a continuation, of application Ser. No. 518,290 filed on July 28, 1983 now abandoned.

The present invention relates to a fluid flow regulator and relates particularly, although not exclusively, to an anaesthesia gas flow regulator.

Anaesthetic gases are usually administered through a "circle". This means that two pipes link the patient with the gas flow regulator, one carrying gas to the patient and the other taking exhaled gas through a soda lime canister which extracts carbon dioxide. Fresh gas is added to the purified gas and the mixture returned to the patient. The gas is usually a mixture of oxygen and nitrous oxide. The circle has a controlled leak to the atmosphere, the gas from which is conducted out of the operating theatre to avoid pollution.

As the only way gas can leave the circuit is by patient uptake, or via the controlled leak, and as the total volume of the circuit is constant, fresh gas must be added to the circuit at a rate equal to the sum of the uptake and the leak. It is usual to add 1.5-3 liters of oxygen and 3-6 liters of nitrous oxide per minute to the circuit. Oxygen is taken up at a constant rate of 250 ml per minute. The rate of uptake of nitrous oxide diminishes with time, commencing at 2.7 liters per minute and falling to 100 ml per minute in 100 minutes. Therefore wastage is in the range of from about 3 to about 7 or 8 liters per minute. Other losses may occur e.g. it the gas carries other substances, including volatile anaesthetics, equivalent fractions of these may be lost as well. Thus percent loss can be up to 90%.

Attempts have been made to reduce such waste and consequent pollution by using a so-called "closed circuit". In this technique, the circuit has no leak, and both nitrous oxide and oxygen are replaced at the rate they are taken up, so as to keep constant both the volume and the ratio of the two gases in the mixture. Oxygen is added at the assumed uptake rate, say 250 ml per minute. In this way, the amount of oxygen in the system should remain constant but as the volume of nitrous oxide changes, so does the percentage of each gas. Oxygen concentration needs to be kept constant. In an effort to achieve this, an "in line" oxygen analyzer has been put in the expiratory limb of the circuit and the oxygen flow rate adjusted according to the meter reading. Nitrous oxide flow rate is adjusted to keep the volume constant. These adjustments are time consuming and inconvenient, therefore most anaesthetists tend to avoid closed circuit techniques.

Accordingly it is an object of the present invention to provide a gas flow regulator which requires minimal supervision and will automatically regulate the oxygen concentration.

A further object is to provide a gas flow regulator that does not require manually controlled oxygen and nitrous oxide flow meters.

With these objects in view the present invention in one aspect provides a fluid flow regulator including, a plurality of actuatable valves and circuit means responsive to a plurality of signals for selective actuation of said valves.

Preferably two valves are provided and said circuit means allows only one of said valves to open at any one time. The circuit means may be coupled to at least one switching device which affects the actuation cycle of said valves.

In a further aspect of the invention there is provided an anaesthetic gas flow regulator control means including, a plurality of electrical outputs for controlling the actuation of valves for flow of oxygen and anaesthesia gas, said control means providing an "oxygen" signal when a predetermined oxygen concentration has been reached and a "volume" signal when oxygen or anaesthesia gas is required, said "oxygen" and "volume" signals being gated to provide an output to one of said valves to cause flow of either oxygen or anaesthesia gas.

In order that the invention may be clearly understood and readily put into practical effect, a preferred non-limitative embodiment of a gas flow regulator constructed in accordance with the invention will now be described with reference to the accompanying drawings in which.

To assist in the understanding of the preferred embodiment a brief description of the regulator will be given before particularly describing the embodiment. The function of the regulator is to supply nitrous oxide and oxygen to an anaesthetic circle so that when the circuit is totally closed, circuit volume and oxygen concentration are maintained automatically. The device works equally well with controlled (I.P.P.V.) or spontaneous ventilation (SV). Incorporated within the invention but functionally distinct from the regulator is a servo system which controls the concentration of volatile adjuvent (VA) in the circle.

A standard digital clocking system records the times for which each of three valves has been open. As the flow rates are fixed, total gas flow over any period may be estimated. The clocking system is not described as its use is only for research purposes.

Gas is supplied by a high flow and a low flow oxygen valve and a high flow and a low flow nitrous oxide valve. Logic circuits select which valve is opened and for how long. There are two interreacting logic circuits, volume logic and oxygen concentration logic.

The control panel is divided into three parts, one for the control of each function - timing (not shown); circuit volume and oxygen concentration; and VA concentration.

Figure 3:
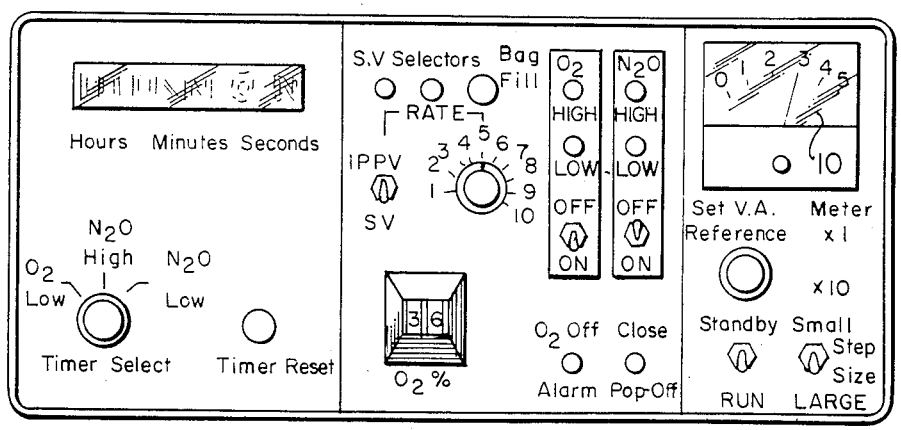
FIG. 3 is the front display panel of the anaesthesia gas flow regulator.

To obtain a general overall understanding of the invention reference is made to FIG. 3 where the front display panel of the regulator is shown. The left hand portion of the panel is to do with the digital clocking system. The "RESET" button resets all three clocks simultaneously. The selector switch selects the display to show the accumulated times of opening for the selected valve. The clocks read up to ten hours in hours, minutes and seconds, with an accuracy of ±0.05 sec.

The middle part of the panel relates to the regulator itself. In the top left hand part of this section are two LEDs. These indicate the function of the SV volume logic. The "BAG FILL" button to their right overrides the volume logic so that gas appropriate to an oxygen analyzer reading is delivered to the circuit until the button is released.

Lower and to the left is the "VENTILATION MODE" switch. This selects either I.P.P.V. or SV volume sensors to active the volume logic. The calibrated knob to its right and below the "BAG FILL" button controls a delay in the volume sensing circuit.

Below is the oxygen reference input. The number displayed on the thumb wheels is the concentration of oxygen which the logic will seek.

Further to the right are two vertical areas in each of which are two LEDs, one above the other over a respective toggle switch. The LEDs indicate which valve is operating with the upper LEDs for the high flow valves and the lower LEDs for low flow valves. The switch is the gas "ON/OFF" switch. The left hand panel is for oxygen whereas the right one is for nitrous oxide. There are two LEDs below the switches. The left hand one is the "OXYGEN OFF" alarm which flashes red if the nitrous oxide switch is switched on when oxygen is off, or when oxygen is switched off when nitrous oxide is on. At the same time an audible alarm sounds. When either of these illegal modes is attempted, the logic continues in the previous legal mode until another legal mode is initiated. The right hand LED is marked "CLOSE POP-OFF".

The right hand panel relates to the VA servo. The knob below the left hand end of the meter controls the position of the pointer on the scale. It is marked "SET V.A. REFERENCE". The servo will attempt to maintain a reading on the VA analyzer to match the reading on this scale. The switch below the knob is the VA servo mode switch. It is marked "STANDBY/RUN". When it is set to run, the servo becomes operational. Of the two switches in the lower right of the panel, the upper one controls the sensitivity of the meter, from 0.5% full scale deflection in the up position to 5.0% full scale deflection in the down position. The servo moves the vaporizer setting in steps. The lower switch selects the step size. Neither of these switches need be shifted from the "UP" position in use.

The volume and concentration logic are integrated so that at all times the concentration logic enables (selects) one set of valves, either oxygen or nitrous oxide. When the volume logic indicates that volume is required, gas is supplied from the appropriate valve. This controls volume and oxygen concentration simultaneously.

The VA servo is driven by a comparator which classifies the concentration of VA as either higher, equal to or lower than the VA reference. If it is higher, the servo shifts the vaporizer control "down". If it is lower, the control is shifted "up". If they are equal, no action is taken.

Figure 1:
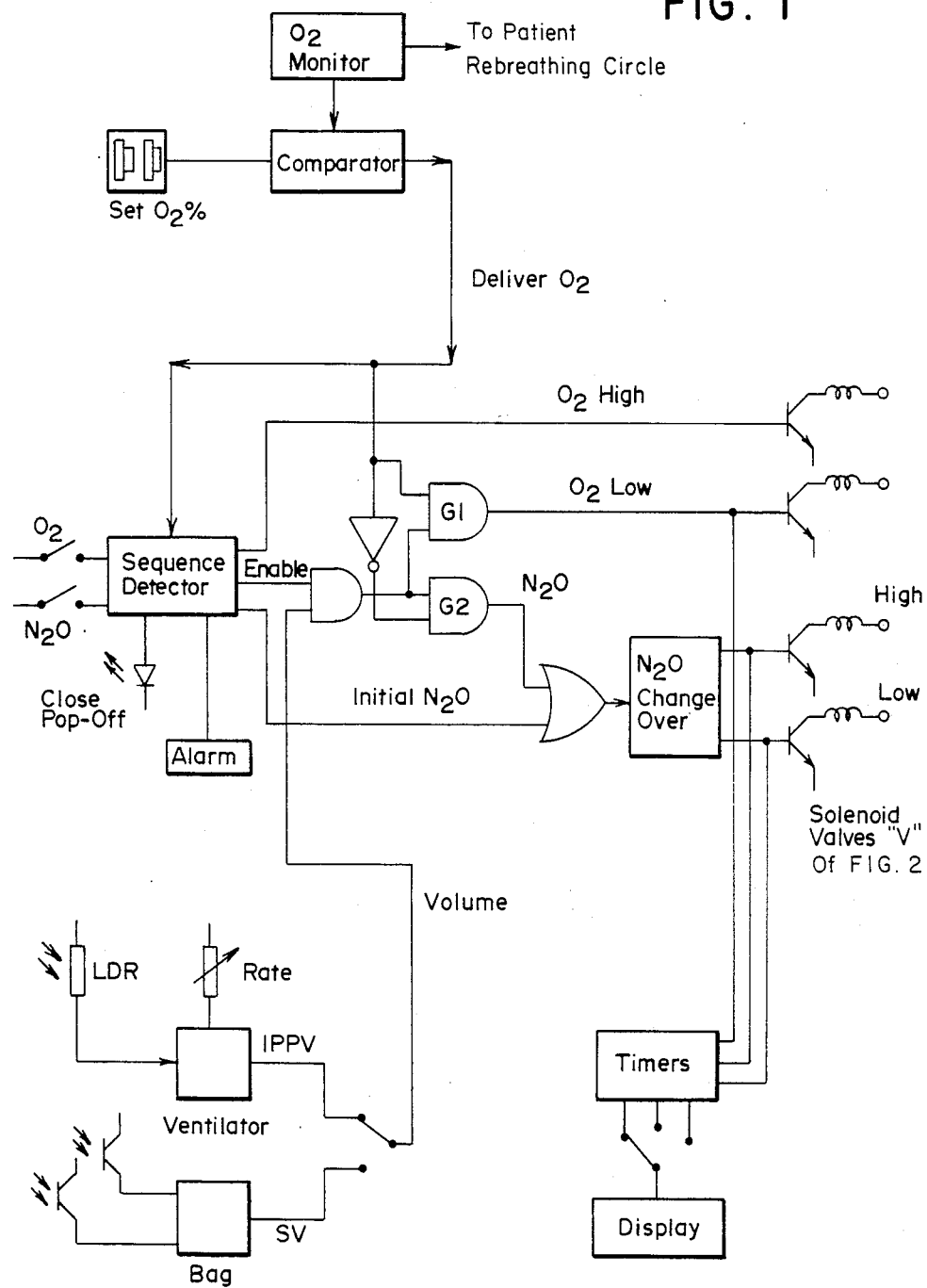
FIG. 1 is a functional schematic diagram of an anaesthesia gas flow regulator made in accordance with the invention.

FIG. 1 shows a functional schematic diagram of the regulator where the critical components are gates G1 and G2. These gates have two inputs, Volume and Concentration (Deliver Oxygen). The system works such that if volume needs replenishing, either oxygen or nitrous oxide will be delivered depending on the logic level of the "Deliver Oxygen" line. The operator sets the percentage of oxygen he wishes to maintain on the front panel BCD thumbwheel switch (See FIG. 3). A conventional electronic oxygen analyzer measures the actual oxygen concentration. These two values are compared to drive the "Deliver Oxygen" line.

The "Volume" line is derived from one of two possible sources. For spontaneous ventilation (S.V.) the volume of a rebreathing bag is measured by two phototransistors. For mechanical ventilation (I.P.P.V.) an LDR (light dependant resistor) determines when the bellows is full. A rate control is provided to ensure that gas is delivered only during the post expiration pause. The front panel switch I.P.P.V./S.V. selects the appropriate logic for the ventilation method being used.

Front panel switches are provided for oxygen and nitrous oxide ON/OFF. These switches are connected to a sequence detector which ensures that switch settings are hazardous to the patient are ignored by the control logic. In these cases the alarm, audible and visual, will be turned on. The main output from the sequence detector is the "volume enable" line. Also provided is the drive for the high flow oxygen valve for pre-oxygenation, and drive for the initial delivery of nitrous oxide. The "Close Pop-Off" LED inidicates to the operator when the circle should be closed.

Gate G1 drives the low flow oxygen valve whereas G2 drives a timing circuit. The timing circuit changes the flow from nitrous oxide High to nitrous oxide Low when correct flow rates can no longer be maintained with the high flow nitrous oxide valve.

Not fundamental to the system, but provided for research purposes are three timers. They monitor the ON times of the high and low flow nitrous oxide valves and the low flow oxygen valve. They display an accumulated total time for the flow of each valve on a common display.

Figure 2:
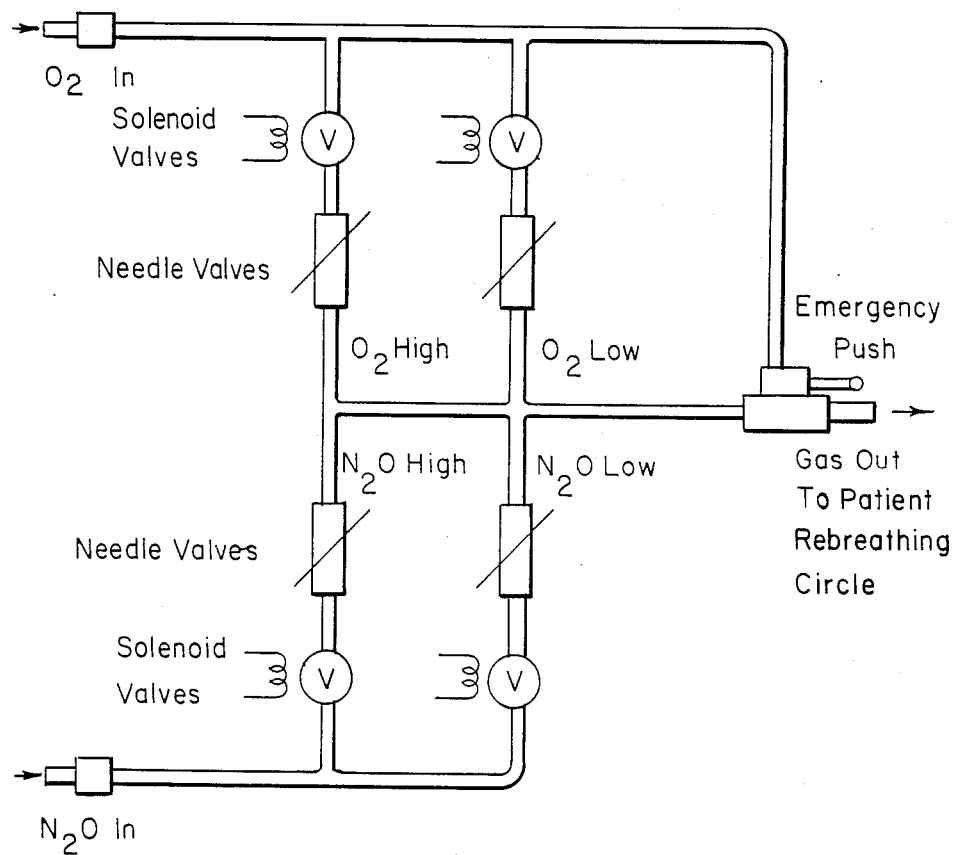
FIG. 2 shows the interconnection of the gases to the regulator of FIG. 1.

The interconnection of the nitrous oxide and oxygen gases is shown in FIG. 2. This figure shows the four solenoid valves shown in FIG. 1 and the manner in which they are coupled together so that at any one time only one valve will be opened. For emergencies, an override valve labelled "EMERGENCY PUSH" is provided to allow oxygen to be supplied at all times, irrespective of the solenoid valve actuated.

Although the problems of automation of volume and oxygen concentration in a closed circle have now been solved by the invention, there remains the problem of providing a controlled concentration of volatile anaesthetic. The solution which has long been used is to put the vaporizer in the circle rather than in the fresh gas line. When this is done, the input to the vaporizer contains expired air and hence anaesthetic vapor. This may lead to a sprialling build up of concentration. As well, the system is subject to sudden dilution of anaesthetic when there is an influx of fresh gas.

These difficulties can be overcome according to this embodiment by a servo system, averaging over 20 seconds, controlling the conentration of volatile agent. This is done by using the output of a conventional "Engstrom EMMA" volatile agent monitor to cotrol the loop. The servo drives the vaporizer inside the circle.

Figure 4:
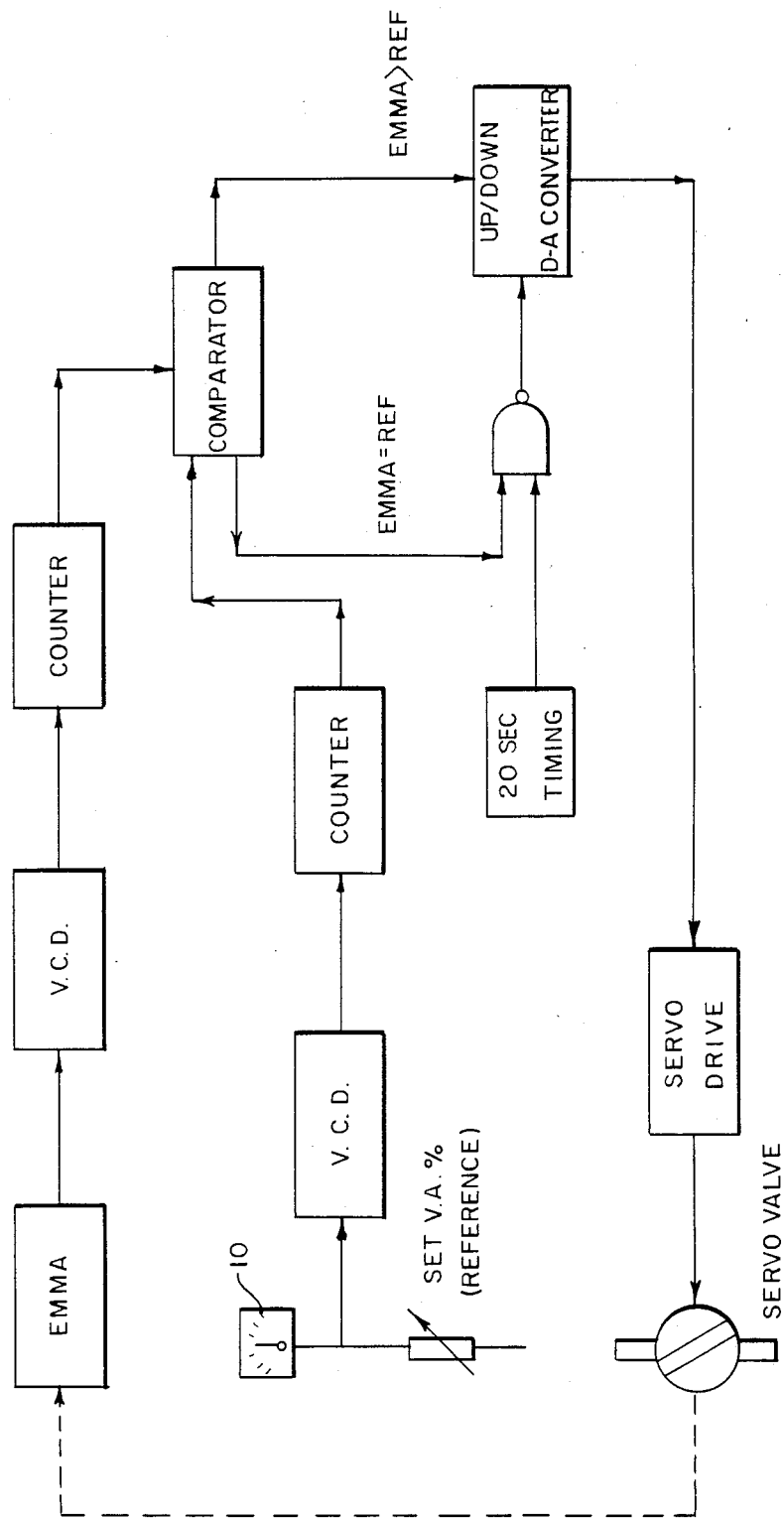
FIG. 4 is a functional schematic diagram of the volatile agent control board of the regulator.

FIG. 4 shows a functional schematic diagram for such volatile agent control which is independent of the gas flow control. The volatile agent monitor or EMMA 10 is connected to a voltage controlled oscillator (V.C.O.). Connected to another V.C.O. is a front panel "SET V.A. REFERENCE" (See FIG. 3). This setting is indicated on an analogue meter movement 10. The frequency output of each V.C.O. is dependent on the voltage at its input. If the two input voltages are equal, then the output frequencies will also be equal. The output of each V.C.O. is connected to two 14 bit binary counters which count up for 20 seconds. At the end of this time the counter outputs are compared. The outputs of the comparator are connected to a 6 bit up-down counter configured as a digital to analog converter. The converter output is applied to a pulse generator circuit which in turn drives the motor connected to the vaporizer concentration control. When the count from EMMA is equal to the reference count, the clock to the D to A converter is inhibited. Thus the analog output voltage remains unchanged as does the position of the vaporizer control. If the monitor reading is greater than the reference count, the D to A converter decrements and the analog output reduces, the control then closes one step. If on the other hand the monitor reads less than the reference, the control opens one step. In this way, the concentration of volatile agent is maintained.

Figure 14:
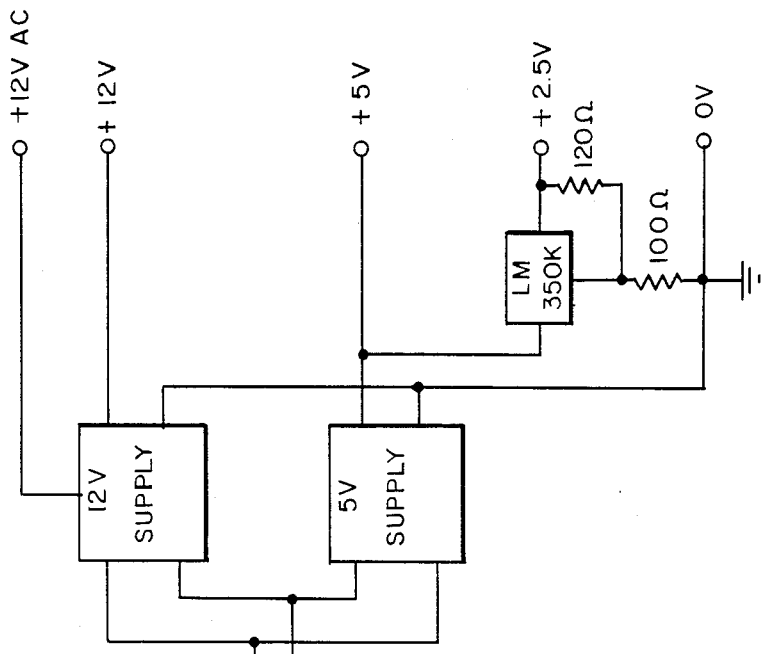
FIG. 14 shows the power supply for the regulator.
Figure 13:
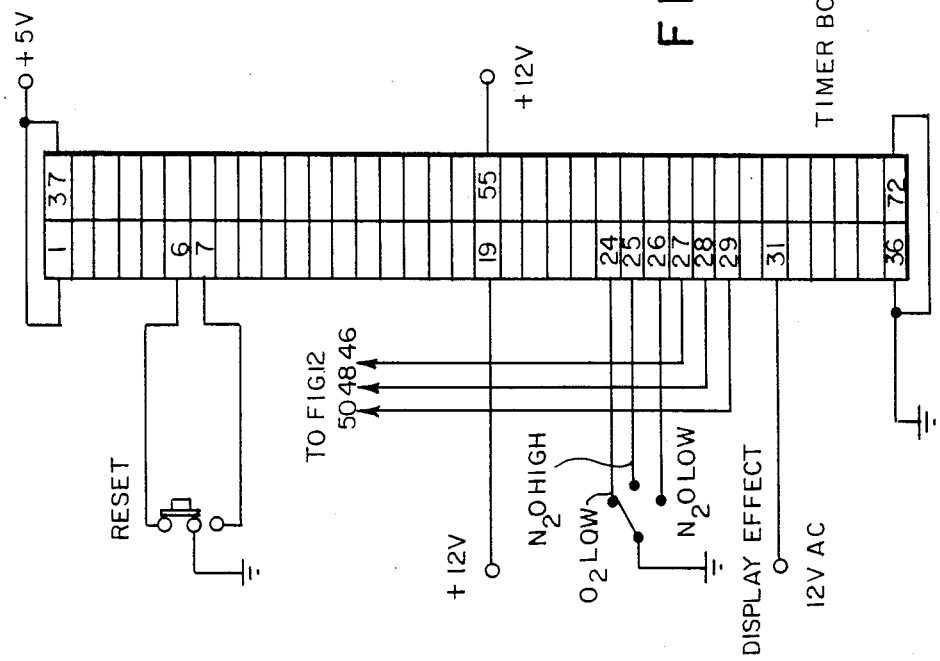
FIG. 13 is a third part of the motherboard for a timer board (not shown) shown only for understanding of the front display panel shown in FIG. 3.

A detailed description of the invention will now be given. An electronics cabinet contains the three plug-in circuit boards, one each for Gas Control (FIGS. 9A to 9D), Volatile Agent Control (FIGS. 10A to 10C) and Timing (not shown). The boards are housed in a semi-enclosed card frame. Also contained in the cabinet are two Power-One D.C. power supplies one 5 v and one 12 v shown in FIG. 14. All the controls are mounted on the front panel and all the iput-output connectors on the rear panel. The rear panel also houses the solenoid drive transistors and the 2.5 v regulator. This regulator supplies power to the globes mounted in the ventilator and on a bag cradle.

The gas control board shown in FIGS. 9A to 9D can be divided into four sections, namely: oxygen analyzer, volume analyzer, sequence detector and nitrous oxide changeover. These sections will be described in turn.

(a) OXYGEN ANALYZER SECTION

Figure 15:
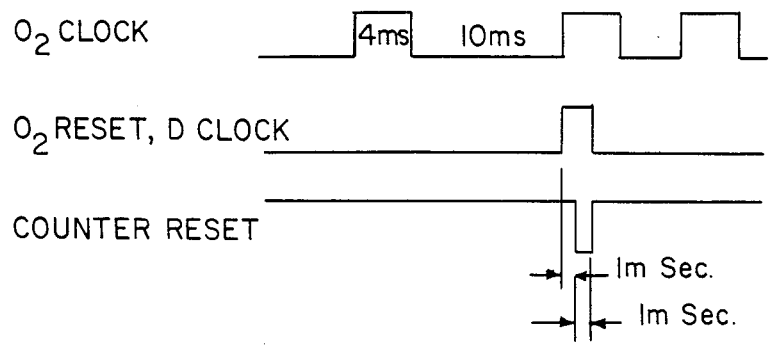
FIG. 15 is a timing diagram for the gas control boards of FIGS. 9A to 9D.

This circuit runs at 5 v and is interfaced to the rest of the controller by transistor Q5 powered at 12 v. Two inputs are provided by the conventional electronic oxygen analyzer. They are labelled Oxygen Clock and Oxygen Reset. They are applied to Z12, a 74C901 CMOS to CMOS buffer. The clock pulses are counted by Z13 and Z14 decade counters whose outputs are sampled at Oxygen Reset time by Z15 and Z16 (D flip flops). Only the measured oxygen concentration is available at the output of the flip flops. The oxygen reset pulse is delayed to provide a counter rest which zeros the counters to enable the next pulse train to be computed. This timing is shown in FIG. 15.

The outputs of the D flip flops are applied to Z17 and Z18 forming a 8 bit binary magnitude comparator. Also applied to the comparator are the outputs of a two decade BCD thumbwheel switch mounted on the front display panel (FIG. 3). Here the operator sets the desired oxygen concentration. The A>B output of the comparator is inverted and buffered by transistor Q5 to provide the "Deliver Oxygen" output to the other sections. A high level is present at this output if the measured percentage of oxygen is too low.

(b) VOLUME ANALYZER SECTION

Figure 5:
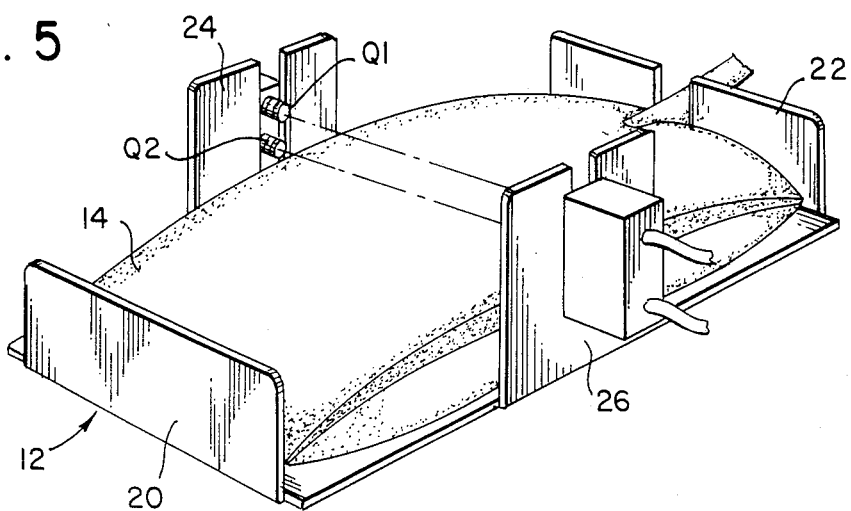
FIG. 5 is a perspective view of a rebreathing bag and associated light sensitive devices for use under spontaneous ventilation.
Figure 6:
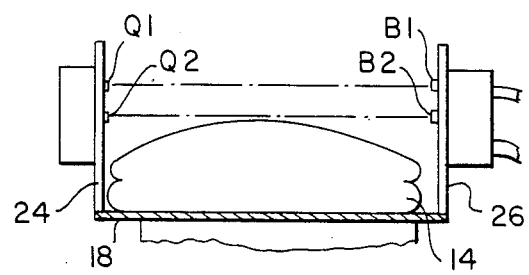
FIG. 6 is a cross-sectional view of FIG. 5.

This circuit provides one output, "Volume". Selection is made on the front panel for S.V. or I.P.P.V. For S.V. two phototransistors Q1 and Q2 drive Z1, 74C00 NAND gates. Q1 and Q2 are mounted on the frame 12, with Q1 and Q2. Reference to FIGS. 5 and 6 illustrates a rebreathing bag 14 sitting within frame 12 having a base 18, end walls 20 and 22 and support members 24 and 26. Phototransistors Q1 and Q2 are adjustable along support member 24 while corresponding globes B1 and B2 are adjustable along support member 26. For pin 6 of Z1 to go high both Q1 and Q2 must be on. This level remains high until both phototransistors are off. Hence for "Volume" to go high, the bag must deflate past Q2. It remains high until the bag is inflated past Q1. The positions of Q1 and Q2 are adjustable on support member 24 to cater for different tidal volumes. Transistors Q3 and Q4 drive front panel LEDs across the phototransistors Q1 and Q2 to allow easy verification of the adjustment of the phototransistors and their respective globes on their support members.

Figure 7:
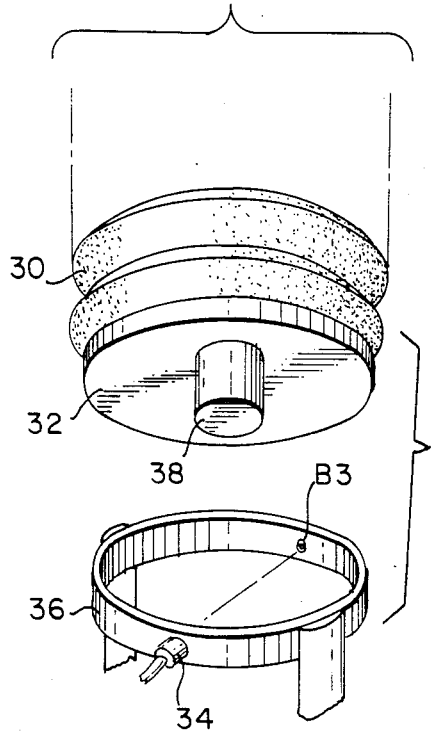
FIG. 7 is a perspective view of a bellows and associated light sensitive device for use under mechanical ventilation (I.P.P.V.)
Figure 8:
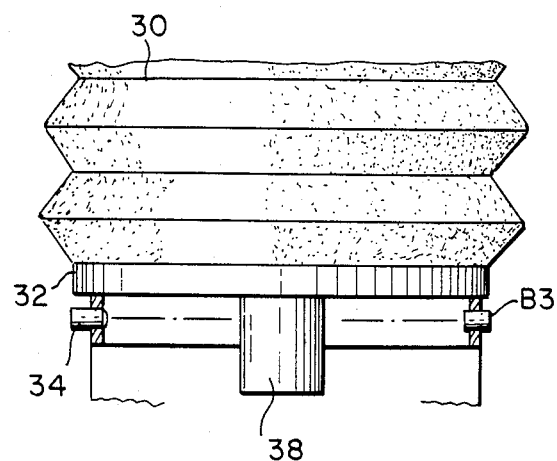
FIG. 8 is a cross-sectional view of FIG. 7.
Figure 9A:
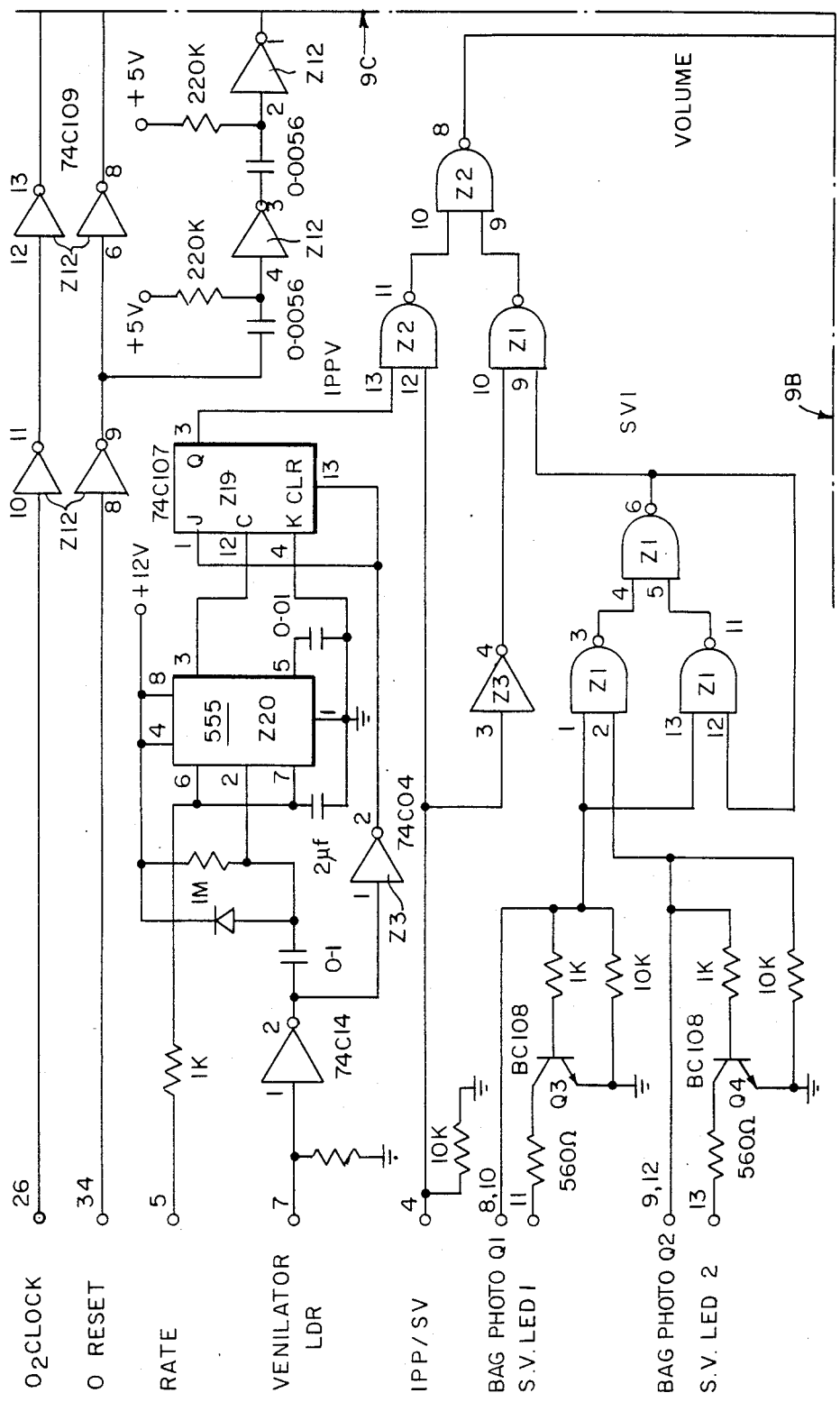
FIGS. 9A to 9D are the circuit schematics for the gas controller board of the regulator.
Figure 9B:
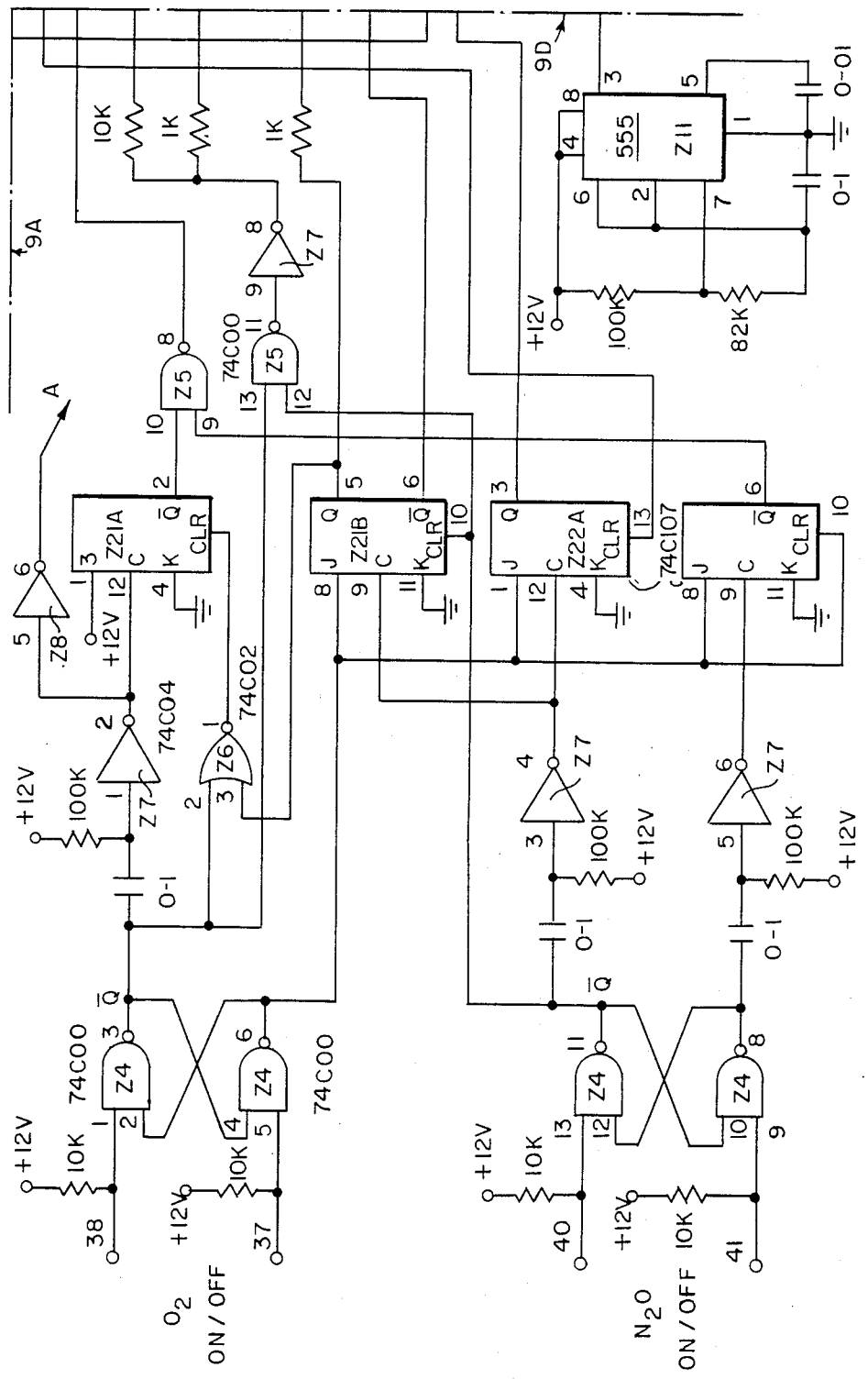
Figure 9C:
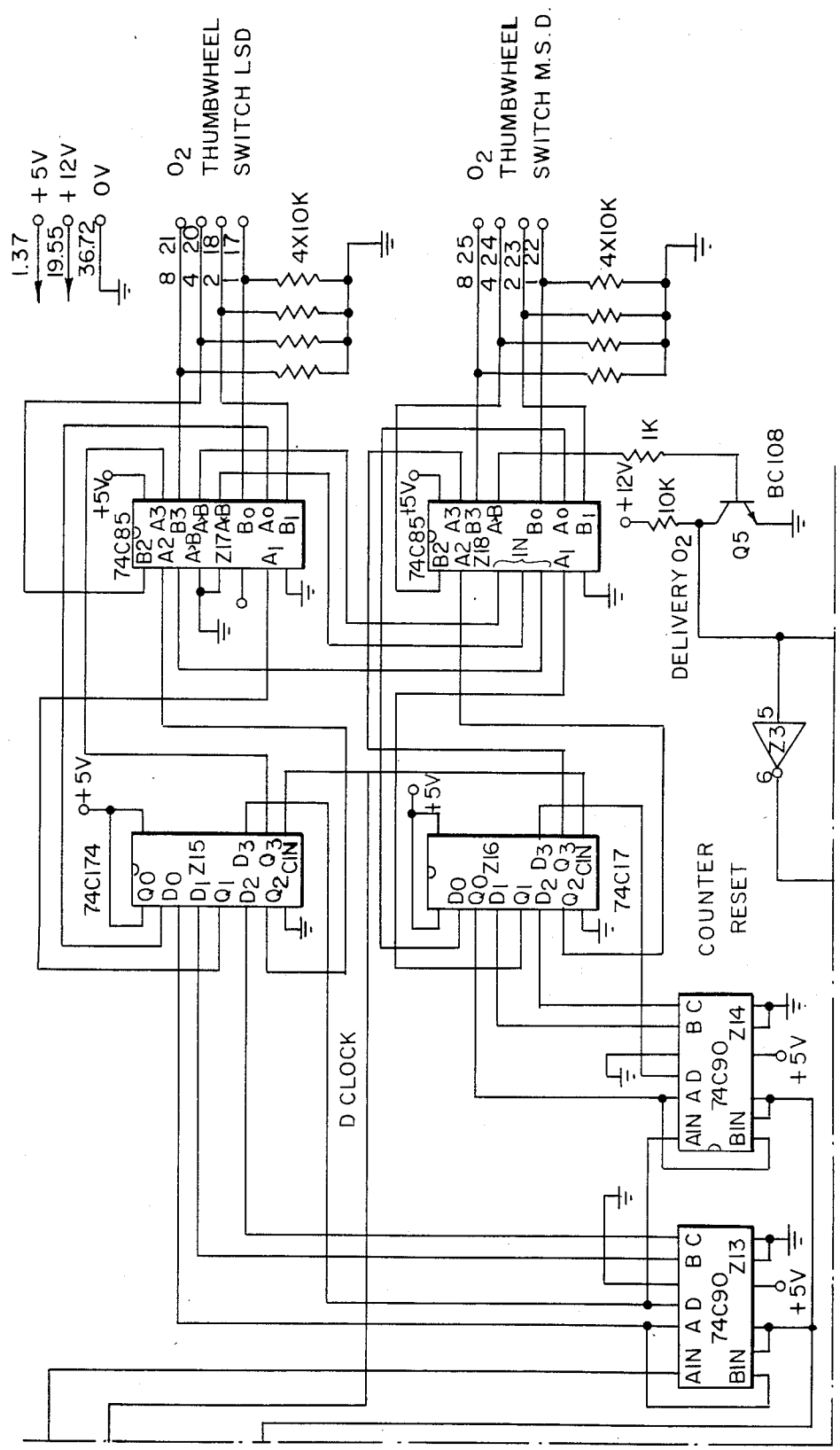
Figure 9D:
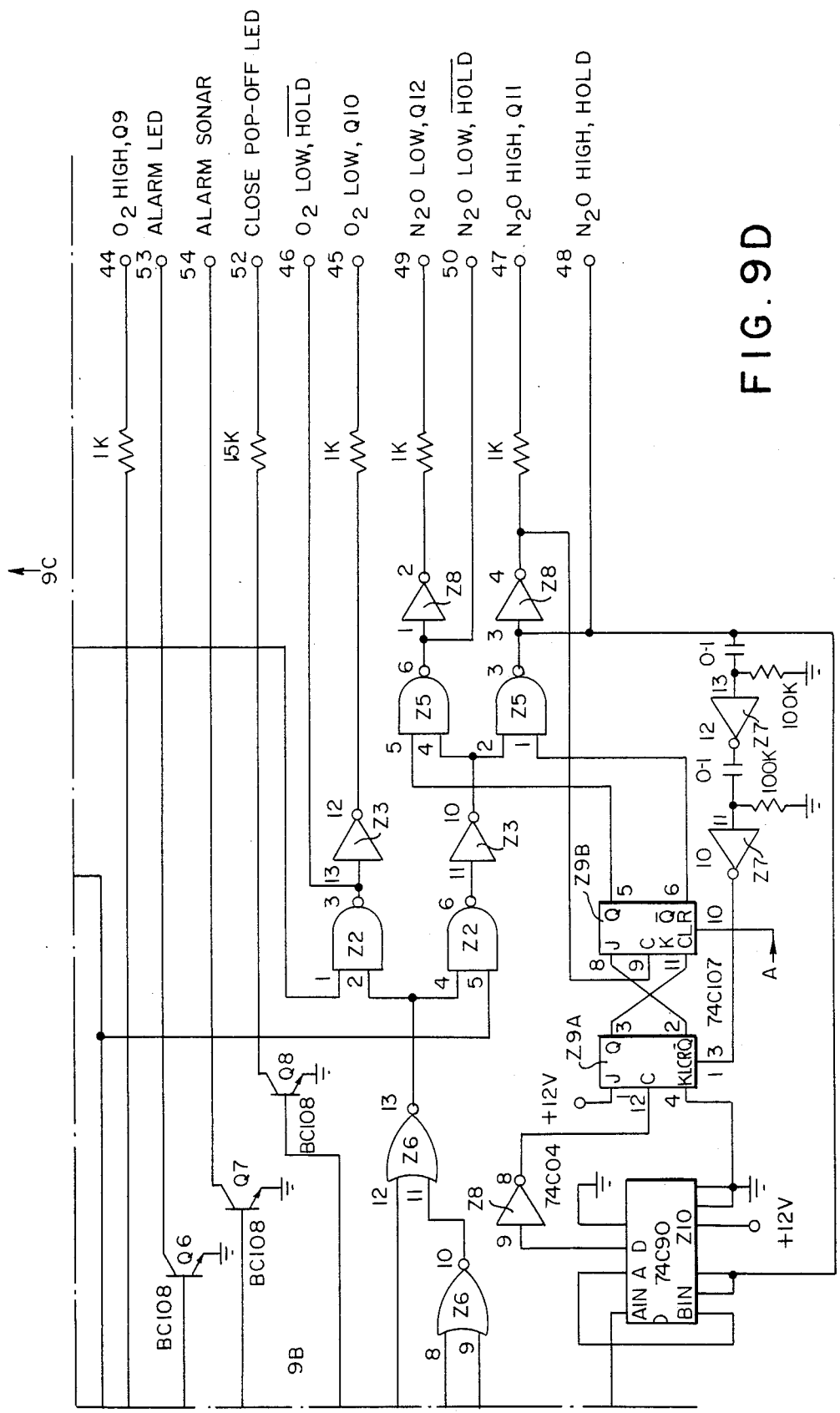

When I.P.P.V. is selected a light dependent resistor (LDR) mounted in the ventilator controls the volume. For correct operation a signal is required to indicate that inspiration has begun. The means of arranging this depends on the design of the ventilator. Reference to FIGS. 7 and 8 shows the ventilator operates by compressing a bellows 30 whose base 32 moves upwardly during inspiration and downwardly during expiration where the downward movement is the phase in which the bellows is refilled.

A light beam is directed horizontally across a diameter of the bellows but just below it by globe B3. The beam is directed onto LDR 34 mounted on ring 36. At the bottom of the bellows a small projection 38 interrupts the beam just before the bellows reaches the end of its downward travel. The LDR 34 drives a 74C14 Schmitt Trigger whose output is taken to Z19 and Z20, a JK flip flop and a 555 Timer respectively. The time out of the 555 is adjustable by the front panel control marked "Rate" (FIG. 3). This delay is adjustable from 0 to 10 seconds. If LDR 34 is still lit after the delay time, the Q output of the flip flop goes high, calling for Volume. The delay ensures that gas will only be delivered during the post expiration pause. This prevents overflow due to exhalation after the bellows have been filled.

(c) SEQUENCE DETECTOR SECTION

Two front panel switches are provided to control the operation of the solenoid valves. They are Oxygen ON/OFF and Nitrous Oxide ON/OFF. Z21 and Z22, with associated gates, ensure that switch settings which may endanger the patient are locked out. The circuit has two alarm outputs which enable a flashing LED and a sonar alarm.

Table 1 shows the logic levels at various points on the circuit for all switch settings. It should be noted that the outputs are a function of the present switch setting and the previous switch setting. It should also be noted that an alarm condition exists whenever nitrous oxide is selected without oxygen also being selected.

Line 1 of the table shows the condition when both switches are off. It also shows that the four solenoid valves are off. This can be considered as the start condition. Oxygen is now switched ON for pre-oxygenation. This brings the high flow oxygen valve ON.

In line three, nitrous oxide is switched ON. This switches the Oxygen High valve Off and enables the nitrous oxide valves. (Nitrous Oxide High comes On as described in the nitrous oxide change-over section description). When the concentration of oxygen comes down to the preset level, line 4 is reached. The volume output is enabled via Z6 (pin 8). This is normal running mode.

When nitrous oxide is switched off, the high flow oxygen comes ON (line 5) until line 6 when oxygen is switched OFF. The circuit is now back in the start condition.

Table 2 shows the circuit response for the two alarm conditions. The first line shows what happens if, from the start condition, the nitrous oxide switch is operated first. The alarm output is enabled but all valves remain off. The alarm is cleared when the nitrous oxide switch is turned off.

The second line shows what happens if, from normal operation (Table 1, line 4), the oxygen switch is turned off. The alarm is enabled but the normal operation of the valves continues. The alarm is cleared by turning the oxygen switch on again.

counter is enabled. The counter is enabled at pins 2 and 3 whenever the high flow nitrous oxide valve is ON. A delayed pulse is also derived from this level which is applied to the clear input of Z9 (pin 13).

When Nitrous Oxide High comes ON, the counter is enabled and flip flop Z9A is cleared. After 100 msecs Z9A is clocked and its Q output goes high. When Nitrous Oxide High switches off, Z9B is clocked. This clocks the J and K inputs in and Z9B $\overline{Q}$ remains high. Therefore the next time nitrous oxide is called for the high flow valve comes on again.

Consider now that Nitrous Oxide High is on for less than 100 msec (as called for by the volume circuit). The counter starts to count up and Z9A is cleared. However, Z9B is clocked before Z9A is clocked. Therefore a logic high is applied to Z9B J. Z9B Q now goes high enabling the low flow rate valve. As there are no further transitions of the high flow output, the circuit will stay in this condition until Z9B is cleared by the Oxygen ON/OFF switch.

Figure 10A:
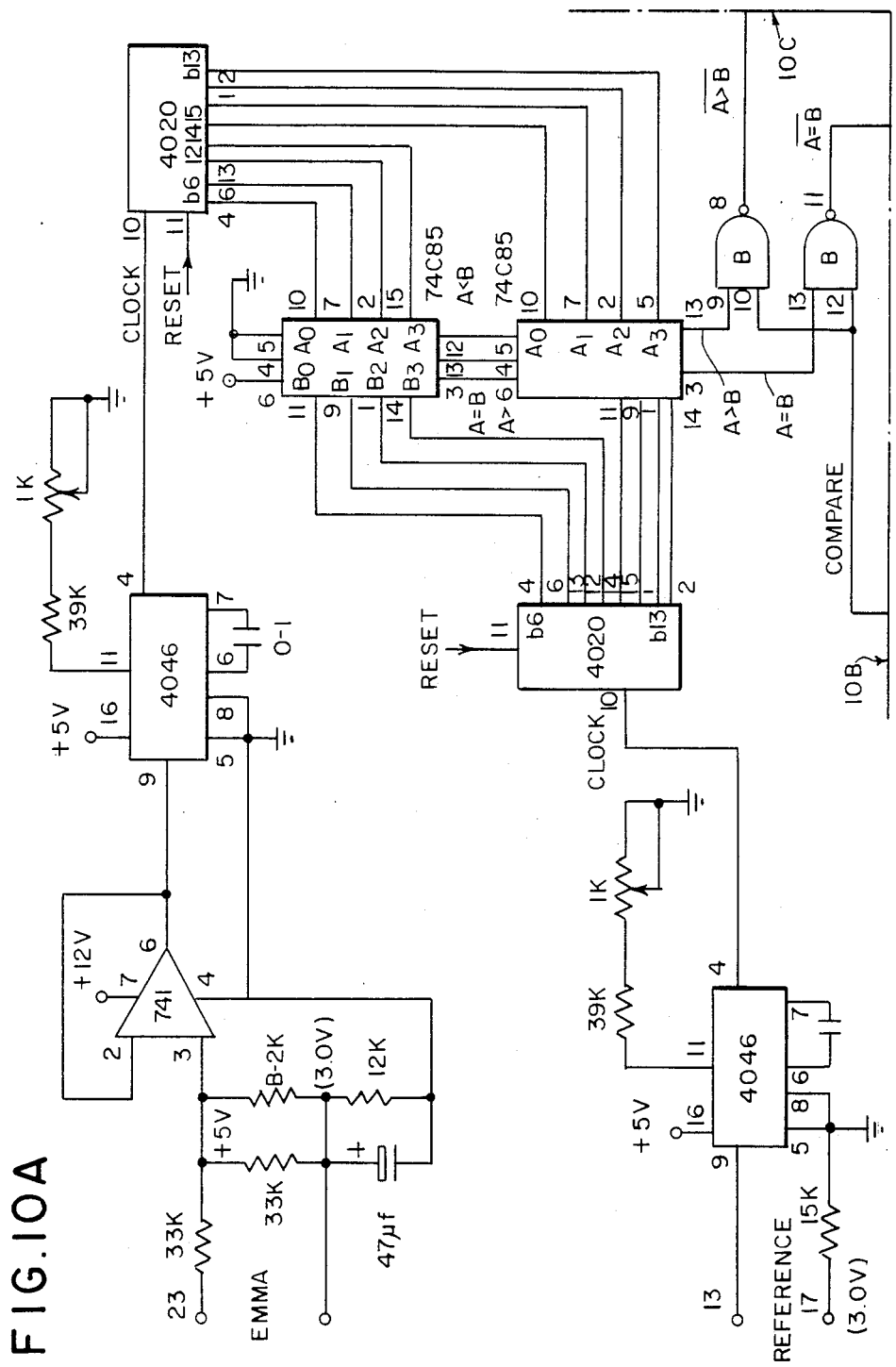
FIGS. 10A to 10C are the circuit schematics for the volatile agent control board of the regulator.
Figure 10B:
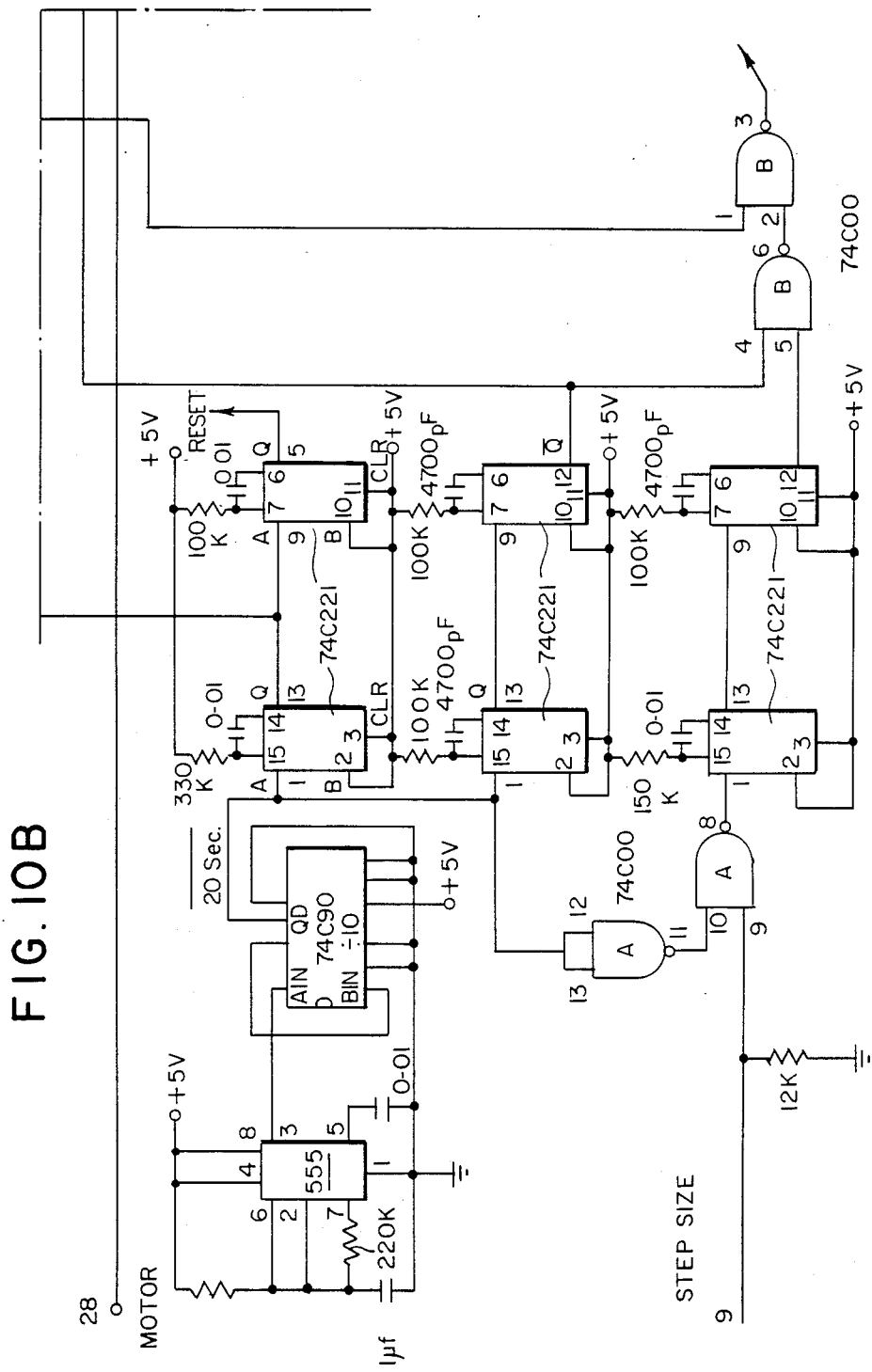
Figure 10C:
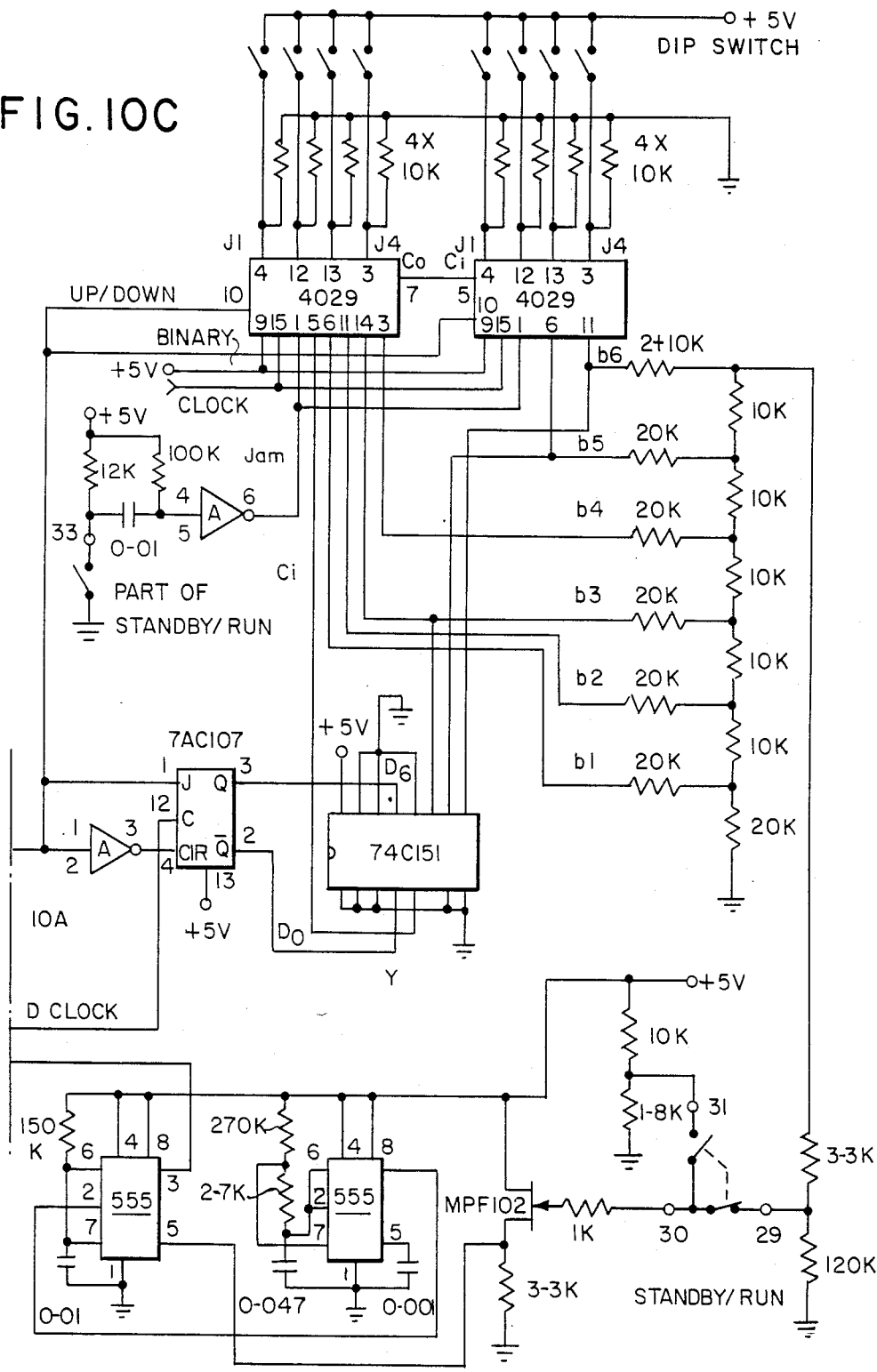

The volatile agent control board shown in FIGS. 10A to 10C will now be described. The conventional Engstrom EMMA volatile agent monitor monitors the percentage of volatile agents in the range 0 to 5%. The recorder output is taken from EMMA and applied to pin 25 and 23 of the board connector. The 1/V % output from Emma is attenuated by 2 and level shifted to a 3 V reference by the 741 op-amp. The output of the 741 is applied to the VCO input of a 4046 Phase Lock Loop (PLL). The level shift is necessary to come within the linear portion of the VCO. Hence the circuit responds

TABLE 1

| | | | | | | | | | | | |
|---|---|---|---|---|---|---|---|---|---|---|---|
| | | | | | SEQUENCE DETECTOR OPERATION | | | | | | |
| Line | SWITCH | | Z21A | Z21B | Z22A | Z22B | Z 5 | | Z 6 | | |
| No | $O_2$ | $N_2O$ | Q | Q | Q | Q | Pin 8 | Pin 10 | Pin 13 | Pin 1 | OUTPUT CONDITION |
| 1 | Off | Off | 1 | 0 | 1 | X | 1 | 0 | X | 0 | 0 | All Values Off |
| 2 | On | Off | 0 | 0 | 1 | X | 1 | 1 | X | 0 | 1 | $O_2$ High On |
| 3 | On | On | 1 | 1 | 0 | 1 | 1 | 0 | 0 | 1 | 0 | $N_2O$ High On ($O_2$% still high) |
| 4 | On | On | 1 | 1 | 0 | 0 | 1 | 0 | V | V | 0 | Normal Operation |
| 5 | On | Off | 1 | 0 | 1 | 0 | 0 | 1 | X | 0 | 1 | $O_2$ High On |
| 6 | Off | Off | 1 | 0 | 1 | X | 1 | 0 | X | 0 | 0 | All Values Off |

1 = Logic High
0 = Logic Low
X = Don't Care
V = Volume

TABLE 2

| | | | | | | | | | | | |
|---|---|---|---|---|---|---|---|---|---|---|---|
| | | | | SEQUENCE DETECTOR UNDER ALARM CONDITIONS | | | | | | | |
| Line | SWITCH | | Z21A | Z21B | Z22A | Z22B | Z 5 | | Z 6 | Z 7 | |
| No | $O_2$ | $N_2O$ | $\overline{Q}$ | Q | $\overline{Q}$ | Q | $\overline{Q}$ | Pin 8 | Pin 10 | Pin 13 | Pin 1 | Pin 8 | OUTPUT CONDITION |
| 1 | Off | On | 1 | 0 | 1 | X | 1 | 0 | X | 0 | 0 | 1 | All Values Remain Off Alarm On |
| 2 | Off | On | 1 | 1 | 0 | 0 | 1 | 0 | V | V | 0 | 1 | Normal Operation Continues Alarm On |

(d) NITROUS OXIDE CHANGE-OVER SECTION

Due to the large variations in the uptake of nitrous oxide two valves are provided with linear flow rates set at 7 L/min. and 4 L/min. When the sequence detector calls for nitrous oxide, pins 2 and 4 of Z5 go high. Selection of which valve comes on is determined by the state of JK flip flop Z9. The second half of Z9 is cleared by transitions of the Oxygen ON/OFF front panel switch. This puts a high on pin 6 of Z9 which ensures that the high flow valve comes on in the first instance. A 555 bistable multivibrator Z11 provides 10 msecs clock pulses to a 74C90 decade counter 210 and this provides a clock pulse to pin 12 of Z9 at 100 msec provided the to 0 to 4% volatile agent. For 3 to 5 V input, the VCO runs from about 110 to 350 Hz. A 1K multiturn trimpot is provided to trim this range. The VCO provides the clock input to a 4020 14 stage binary counter.

Figure 11:
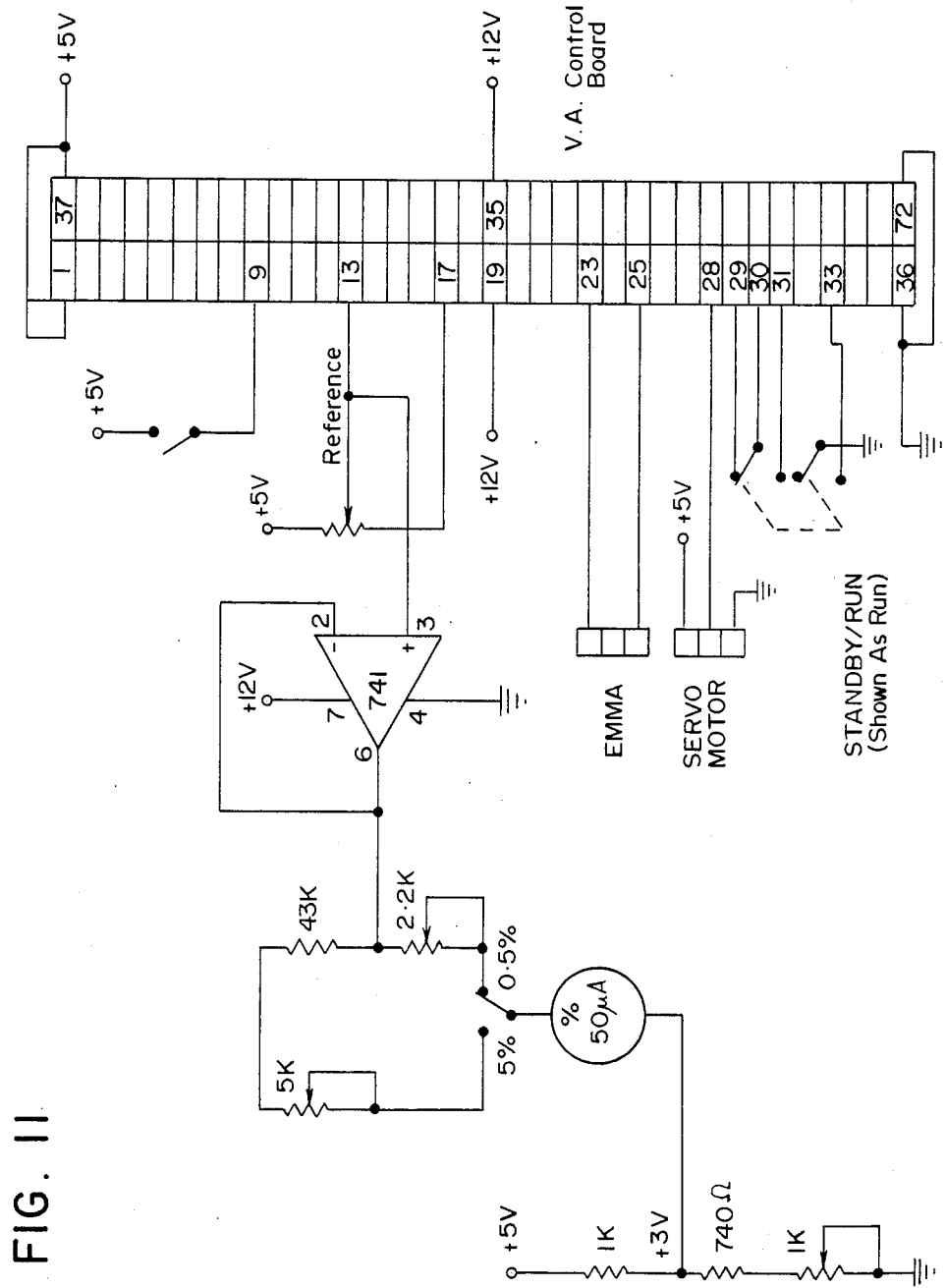
FIG. 11 shows a first part of the motherboard for the volatile agent control board of FIGS. 10A to 10C.
Figure 12:
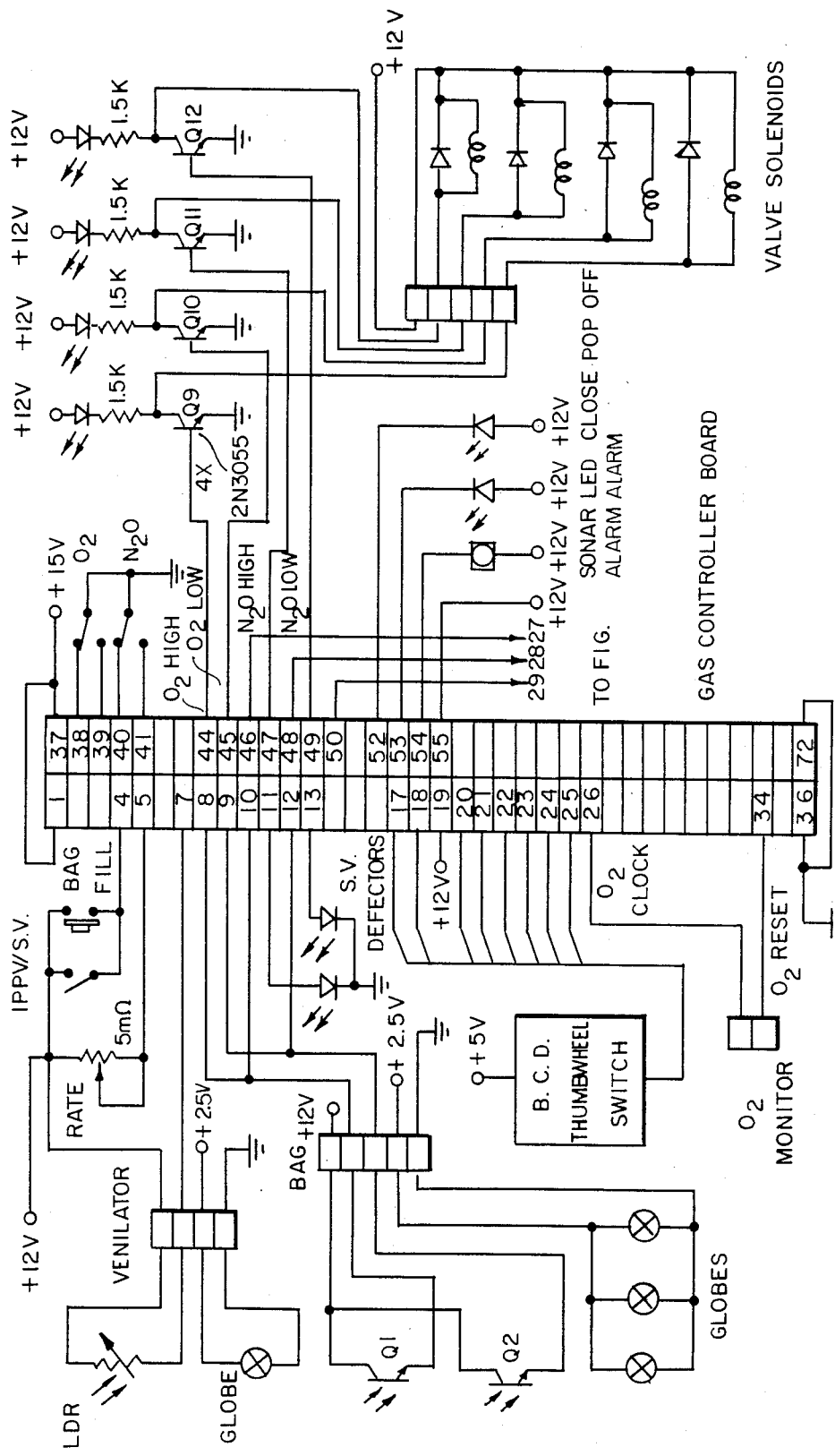
FIG. 12 is a second part of the motherboard for the gas controller board of FIGS. 9A to 9D.

The reference control feeds the reference meter circuit and another 4046 PLL. The meter has two ranges, 0 to 0.5% and 0 to 5%. The 4046 is configured exactly the same as to 4046 in the measure circuit and is shown in FIG. 11. It also feeds a 4020 counter.

Eight outputs, b6 to b13, are taken from the counters and feed two 74C85 chips configured as an 8 bit magnitude comparator. Two outputs A=B and A>B are taken from the comparator and applied to NAND gates where they are gated with a COMPARE timing signal. The resulting A>B signal is applied to the up/down control line of two 4029 up/down binary counters. In conjunction with an R-2R resistor network these counters form a 6 bit digital to analog converter. Also coupled to this counter is an 8 bit dip switch to the jam inputs. This allows a predetermined value to be present in the counter. This number is entered into the counter whenever the "standby/run" switch is put into the Run position.

The A>B signal is fed also to half of a 74C107 flip flop configured as a D flip flop, whose outputs feed a 74C151 eight channel digital multiplexer. The operation of the multiplexer will be explained later. The output of the D to A converter is buffered by an MPF102 JFET and fed to a 555 timer connected as a variable pulse width monostable. Also feeding the monostable is the output of a 555 astable with a pulse repetition rate of about 20 msec. The resultant pulse train from the monostable directly drives a model airplane servo motor which is mechanically coupled to the vaporizer. The position of the servo is related to the pulse width and the PRR is not critical. The vaporizer used in this embodiment is a modified "GOLDMAN" vaporizer.

Part of the Standby/Run switch is connected at the MPF102 and to a voltage divider. In the standby position the output of the D to A converter is disconnected and a bias voltage is applied to the gate. This voltage holds the vaporizer in the closed position.

A 555 timer and a 74C90 decade counter provide basic timing at a 20 second rate. This timing is not critical but is selected to be greater than at least two breath times. This is necessary to overcome small fluctuations in the monitor during inspiration and expiration.

All other timing is derived from the 20 Sec. signal by 74C221 dual monostables. One provides Compare and Reset pulses. The Compare pulse is applied to the outputs of the comparator. As previously discussed the 4020 counters feed the comparator. These are fed from the VCOs and hence represent the average, over 20 seconds of the reference and measure inputs. The outputs of the comparator are therefore only considered valid during Compare time. After this the counters are reset.

Figure 16:
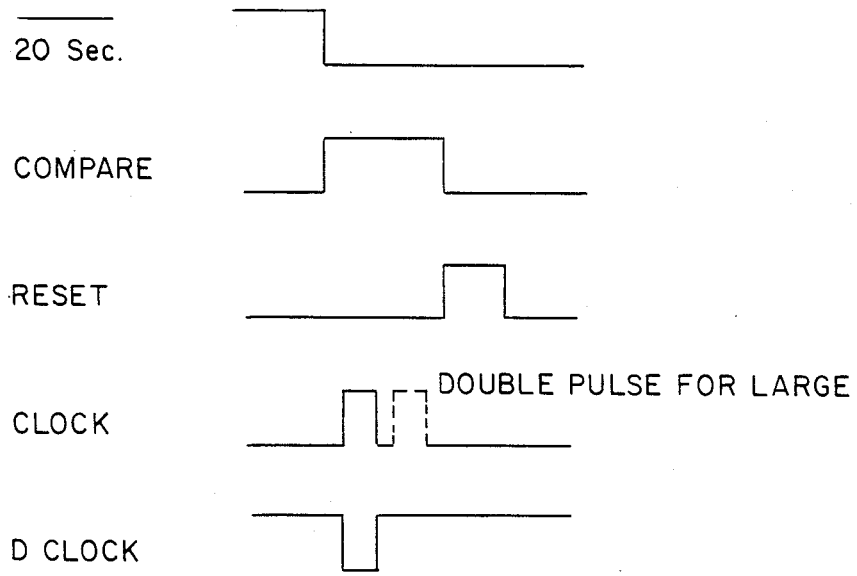
FIG. 16 is a timing diagram for the volatile agent control board of FIGS. 10A to 10C.

Two other outputs are provided from the timing circuit. One is D Clock which gates the A>B level into the D flip flop connected to the 74C151 multiplexer. The other is the clock pulse to the D to A converter. This can in fact be two pulses, determined by the Step Size Switch. For large steps of the servo the D to A increments or decrements twice. FIG. 16 shows the timing diagrams for these pulses. Note that all clock pulses occur when Compare is valid. Also note that the clock is inhibited if A=B.

Simply then, the coparator determines whether the concentration of volatile agent is correct, high or low. This sets up the D to A converter which already holds some count. (This may have just been entered via the jam inputs). If the concentration is OK the counter remains as it is. If A≠B the clock pulse(s) is gated to the counters which increment or decrement. This changes the voltage to the monostable which changes its pulse width. Hence the servo will move to adjust the concentration. Use of a large step size of the servo allows the reference point to be reached quickly, however the servo tends to hunt around the reference point. The circuit should maintain the concentration to within 0.05 vol. % and using small step size very little hunting occurs.

The purpose of the 74C151 multiplexer is to determine whether the servo is at an extreme end of its travel. If it is, the counter is inhibited from counting. This ensures that the counter does not "wrap-around".

Consider the following situation: The servo is full open and the counter is near its maximum count. This situation can occur when the operation has started and the uptake of the volatile agent by the body is rapid. The comparator is still calling for more agent so the counter gets to its maximum count. One more clock pulse causes the counter to count past maximum to zero. The servo now goes fully closed and the volatile agent is cut off. The reverse situation can occur in the down count direction (and is potentially more dangerous). The multiplexer samples the counter output and applies a high logic level to the carry-in input of the first counter when the servo is in its maximum or minimum position. This inhibits the count.

Only three outputs of the counter are needed to determine the servo position, with $b_3$, $b_5$ and $b_6$ being used. These are applied to the data inputs of the multiplexer. When these three bits are all 0, D0 is active. When $b_6=b_5=1$ and $b_3=0$, D6 is active. At these counts the level on the D input is available at the output Y. For all other counts the data inputs are held zero. The level on D0 and D6 is determined by the 74C107 flip flop whose input is the up/down logic level. If the counter is counting up at compare time D6=1, if counting down D0=1.

Consider the counter at $b_6=b_5=1$, $b_3=0$ and the count is in up direction A logic 1 is at Y and further counting in this direction is inhibited. If the direction control now changes to require a down count, the Q output of the flip flop goes zero thus D6=0. This is routed to Y, hence the carry-in input. The counter can now count, but in the down direction only. A similar situation takes place in the minimum position. Thus the servo cannot "wrap around" but can always correct to the reference point.

It is to be understood that modifications in details of design and construction may be made without departing from the spirit and scope of the invention, the nature of which has been set out in the appended claims.

I claim:

1. An anaesthetic gas flow regulator, comprising:
   an oxygen gas flow line adapted to be connected to a supply of oxygen;
   an anaesthesia gas flow line adapted to be connected to a supply of anaesthesia gas;
   first and second controllable valves operatively connected to said oxygen and anaesthesia gas flow lines, respectively;
   patient rebreathing circle means for delivering and exhausting a mixture of oxygen and anaesthesia gas to and from a patient;
   common outlet means, operatively connected to said first and second controllable valves, for combining flow of said oxygen and anaesthesia gas for delivery of a mixture of oxygen and anaesthesia gas to said patent rebreathing circle means;
   oxygen analyzer means for sensing the oxygen concentration of said mixture in said patient rebreathing circle means and for providing an oxygen signal when a minimum predetermined oxygen concentration is sensed by said oxygen analyzer means;

means for sensing the volume of gas in said patient rebreathing circle means for generating a volume signal indicative of a minimum volume threshold value;

control means, responsive to said oxygen and volume signals developed by said oxygen analyzer means and said means for sensing, respectively, and connected to said first and second controllable valves for controlling one of said first and second valves to supply a controlled amount of either oxygen or anaesthesia gas to said rebreathing circle means through said common outlet means, such that the volume in said patient rebreathing circle means is kept constant and oxygen is delivered to said patient rebreathing circle means through said first valve means only when said minimum predetermined signal is sensed by said control means, otherwise anaesthesia gas is delivered to said patient rebreathing circle means through said second valve means to maintain the volume thereof constant.

2. The regulator of claim 1, wherein said means for sensing and generating said volume signal is a ventilator operatively connected with said patient rebreathing circle means, said ventilator including at least one light sensitive device operatively positioned on and resposive to movement of a portion of said ventilator, said ventilator having a spontaneous ventilation mode and a mechanical ventilation mode.

3. The regulator of claim 2, further including upper and lower light sensitive devices disposed in spaced relation above a rebreathing bag, wherein in said spontaneous ventilation mode said light sensitive devices are interrupted by inflation and deflation of said rebreathing bag, said volume signal being generated when said light sensitive devices are both uninterrupted and being terminated when said bag inflates to interrupt said upper light sensitive device.

4. The regulator of claim 2, further including a bellows, wherein in said mechanical ventilation mode said bellows interrupts said light sensitive device and said volume signal is generated a predetermined time after interruption of said light sensitive device.

5. The regulator of claim 1 further including means for activating said oxygen and anaesthesia gas flow lines, and means for assuring that during operation said oxygen flow line cannot be de-activated unless said anaesthesia gas flow line has been de-activated.

6. The regulator of claim 5, wherein alarm means are provided to indicate incorrect activation or de-activation of said oxygen and anaesthesia gas flow lines.

7. The regulator of claim 1, wherein alarm means are provided to indicate incorrect activation or deactivation of said oxygen and anaesthesia gas flow lines.

8. The regulator of claim 1, wherein said first and second controllable valves each include high and low flow rate valves for supplying anaesthesia and oxygen gas to said common outlet means of said regulator and wherein the flow rates of both anaesthesia gas and oxygen are controlled by said high and low flow rate valves which are selectable by said means for controlling.

9. The regulator of claim 1, further including means, responsive to the concentration of anaesthesia gas in said patient rebreathing circle means, for comparing the anaesthesia gas concentration with a predetermined anaesthesia gas concentration and an adjusting means coupled to an output of said means for comparing, for holding the anaesthesia gas in said circle means at a predetermined concentration.

10. The regulator of claim 9, further including a volatile anaesthetic vaporizer for monitoring the percentage of volatile agents in said anaesthetic gas wherein said adjusting means includes a servo motor mechanically coupled to said vaporizer for controlling the concentration of anaesthesia gas in said circle means.

11. The regulator of claim 10, wherein said adjusting means further includes counters which are incremented or decremented to values dependent upon the anaesthesia gas concentration and said predetermined anaesthesia gas concentration, the values of said counters being compared to control the operation of said adjusting means, and an inhibitor for preventing counter wraparound at either end of the servo travel of said servo motor.

12. The regulator of claim 11, wherein upon initial activation or power up of said regulator an initial value is placed in said counters.

* * * * *